United States Patent

Shiroki et al.

[11] 4,169,899
[45] Oct. 2, 1979

[54] PENICILLAMINE COMPOUNDS

[75] Inventors: Masami Shiroki, Nakatsu; Yutaka Maruyama, Yoshitomimachi; Kazuhiro Goto, Nakatsu, all of Japan

[73] Assignee: Yoshitomi Pharmaceutical Industries, Ltd., Osaka, Japan

[21] Appl. No.: 867,413

[22] Filed: Jan. 6, 1978

[30] Foreign Application Priority Data

Jan. 8, 1977 [JP] Japan .................................. 52-1008

[51] Int. Cl.$^2$ .................... A61K 31/54; C07D 279/06
[52] U.S. Cl. ...................................... 424/246; 544/54; 260/347.3; 260/326.43; 546/233; 560/16; 560/153; 562/557; 424/309; 424/311; 424/317; 542/416; 544/400; 544/160; 546/331; 549/76; 549/60; 549/77
[58] Field of Search ........................... 544/54; 424/246

[56] References Cited

U.S. PATENT DOCUMENTS

| | | | |
|---|---|---|---|
| 2,585,064 | 2/1952 | Wheeler et al. | 544/54 |
| 3,732,216 | 5/1973 | Weinstock | 544/54 |

FOREIGN PATENT DOCUMENTS

| | | |
|---|---|---|
| 49-76824 | 7/1974 | Japan . |
| 49-76825 | 7/1974 | Japan . |
| 52-5713 | 1/1977 | Japan . |
| 52-33626 | 3/1977 | Japan . |

OTHER PUBLICATIONS

Cherbuliez et al., *Helvetica Chemica Acta.*, vol. 48, pp. 1414–1423 (1965).

Campaigne et al., *Jour. Medicinal Chemistry*, vol. 7, pp. 132–135 (1965).

*Primary Examiner*—John M. Ford
*Assistant Examiner*—Jane T. Fan
*Attorney, Agent, or Firm*—Sughrue, Rothwell, Mion, Zinn and Macpeak

[57] ABSTRACT

Penicillamine compounds of the formula:

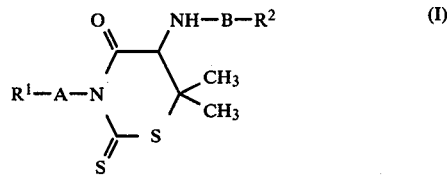

and of the formula:

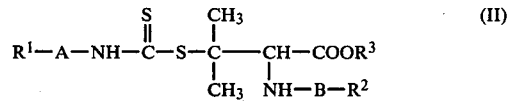

wherein $R^1$, $R^2$, $R^3$, A and B are as defined hereinafter, and pharmaceutically acceptable acid addition salts thereof are disclosed. II are the products of hydrolysis or alcoholysis of I, and I are in turn the products of dehydration of II or alcohol removal form II. I and II are useful for the treatment of rheumatoid arthritis.

17 Claims, No Drawings

PENICILLAMINE COMPOUNDS

This invention relates to novel penicillamine compounds and methods for the manufacture of such compounds.

According to one aspect of the present invention, there is provided a penicillamine compound selected from the group consisting of a cyclic penicillamine compound (tetrahydro-2H-1,3-thiazine compound) of the formula:

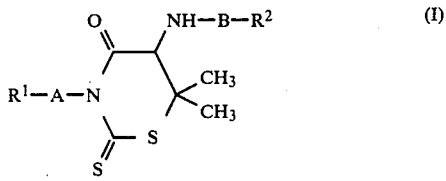

and a penicillamine compound of the formula:

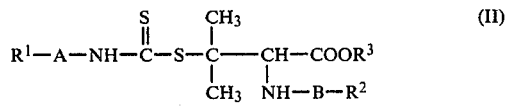

and a pharmaceutically acceptable acid addition salt of a compound of formula (I) or (II).

In the above formulas, $R^1$ represents hydrogen, lower alkyl (e.g. methyl, ethyl, propyl, isopropyl, butyl, isobutyl, sec-butyl or tert-butyl), alkenyl (e.g. vinyl, isopropenyl or 1-propenyl), lower alkoxycarbonyl (e.g. methoxycarbonyl, ethoxycarbonyl or butoxycarbonyl), aryl (e.g. phenyl), diphenylmethyl, heteroaryl (e.g. furyl, thienyl or pyridyl) or a group of the formula: $(R^4)(R^5)N$— wherein $R^4$ and $R^5$ represent each lower alkyl, aryl or aralkyl (e.g. benzyl, phenethyl or α-methylbenzyl), or $R^4$ and $R^5$ together with the adjacent nitrogen atom form a heterocycle (e.g. pyrrolidine, piperidine or morpholine, or piperazine which may be substituted at 4-position by lower alkyl or aryl); $R^2$ represents alkyl (e.g. methyl, ethyl, propyl, isopropyl, butyl, pentyl, hexyl, heptyl, octyl, nonyl, decyl, undecyl or dodecyl), aryl, aralkyl, aralkenyl (e.g. styryl, cinnamyl or α- or β-methylstyryl), aryloxyalkyl (e.g. aryloxymethyl or 1-aryloxyethyl), heteroaryl or heteroaryl-substituted lower alkyl (e.g. heteroaryl-substituted methyl or ethyl); $R^3$ represents hydrogen or lower alkyl; A represents alkylene of 1 to 5 carbon atoms (e.g. methylene, ethylene, trimethylene, tetramethylene, pentamethylene, propylene or 2-methyltrimethylene); and B represents —C(=O)— or —C(=O)O—; in which definitions the term "aryl", "aralkyl", "aralkenyl" or "heteroaryl" in each occurrence means that it may be substituted by at least one substituent at any position(s) on the (hetero)aromatic nucleus, each substituent being independently selected from lower alkyl, lower alkoxy (e.g. methoxy, ethoxy, propoxy or butoxy), halogen (F, Cl, Br or I), nitro, trifluoromethyl, methylenedioxy, lower-alkylsulfonamido (e.g. methanesulfonamido or ethanesulfonamido), arylsulfonamido (e.g. benzenesulfonamido), trifluoromethylsulfonamido, acyl (e.g. acetyl or propionyl) and acetoxy.

Preferred classes of penicillamine compounds of formula (I) or (II) are those wherein $R^1$ is a group of the formula: $(R^4)(R^5)N$— wherein $R^4$ and $R^5$ are as defined above.

The compounds of formulas (I) and (II) can be produced according to the following reaction scheme:

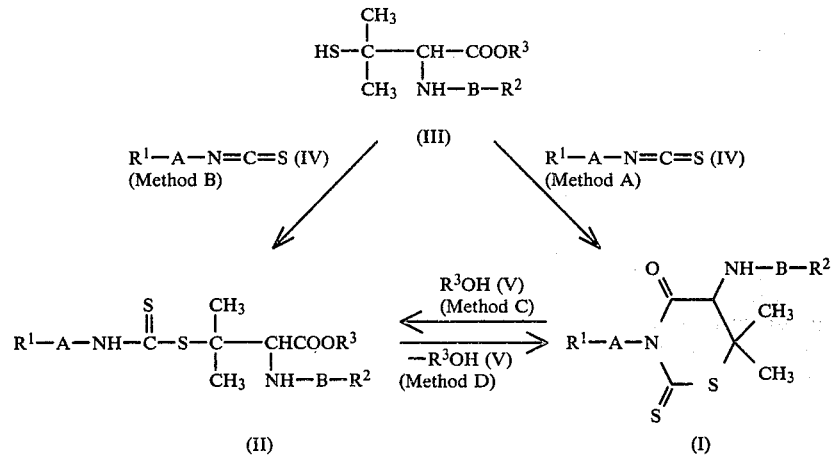

In the above formulas, $R^1$, $R^2$, $R^3$, A and B are as defined above.

METHOD A

The reaction is preferably carried out by bringing each mole of a penicillamine compound (III) into contact with one to several moles, preferably a slightly excess amount of an isothiocyanate compound (IV), in an inert solvent, if necessary in the presence of a condensing agent, at a temperature of from room temperature to about 150° C., preferably about 50° to 100° C., for a period of from several hours to several tens of hours. As a solvent is used an alcohol (e.g. methanol, ethanol, propanol, isopropanol, butanol, isobutanol, sec-butanol, tert-butanol or ethylene glycol monomethyl ether), an ether (e.g. ethyl ether, butyl ether, dioxane, tetrahydrofuran, monoglyme of diglyme), an ester (e.g. ethyl acetate or butyl acetate), an amide (e.g. dimethylformamide or dimethylacetamide), a hydrocarbon (e.g. benzene, toluene, xylene or ligroin), a halogenated hydrocarbon (e.g. chloroform, methylene chloride, carbon tetrachloride, dichloroethane, tetrachloroethane or chlorobenzene), an amine (e.g. pyridine, picoline or dimethylaniline), a ketone (e.g. acetone, methyl ethyl ketone, methyl isobutyl ketone or cyclohexanone) or dimethyl sulfoxide or a mixture thereof. As a condensing agent is used a tertiary amine (e.g. triethylamine, pyridine, picoline, quinoline, N-methylpiperidine or dimethylaniline), a tertiary ammonium hydroxide (e.g. benzyltrimethylammonium hydroxide), a strongly basic anion exchange resin or an acidic substance (e.g. hydrochloric acid, sulfuric acid, hydrobromic acid, acetic acid, p-toluenesulfonic acid, benzenesulfonic acid, thionyl chloride, phosphorus pentachloride, phosphorus trichloride or phosphorus oxychloride).

METHOD B

The reaction of a penicillamine compound (III) with an isothiocyanate compound (IV) is usually carried out under milder conditions than those in Method A, for example, in an inert solvent such as mentioned for Method A, if desired in the presence of a condensing agent such as mentioned for Method A and water, at room temperature or under ice cooling, for a period of from several hours to several days.

METHOD C

Each mole of a cyclic penicillamine compound (I) is preferably reacted with one to several moles of a lower alkanol or water (V), in an inert solvent such as mentioned for Method A, at room temperature or under ice cooling, for a period of from several hours to several days.

METHOD D

The elimination of $R^3OH$ from a penicillamine compound (II) is preferably carried out with or without a solvent such as mentioned for Method A, if desired in the presence of an acidic condensing agent such as mentioned for Method A, at a temperature of from 50° to 150° C., for a period of from several hours to several tens of hours.

Since the compounds of formulas (I) and (II) contain an asymmetric carbon atom, they may be obtained as racemic mixtures or as optical isomers. It is to be understood that the optical isomers as well as racemic mixtures are embraced within the scope of the present invention.

The compounds of formulas (I) and (II) can be converted into acid addition salts with various inorganic and organic acids, for example, hydrochloric, hydrobromic, sulfuric, nitric, phosphoric, maleic, fumaric, succinic, citric, tartaric, methanesulfonic, benzenesulfonic, p-toluenesulfonic and naphthalenesulfonic acids.

The compounds of formulas (I) and (II) and salts thereof exhibit potent antiinflammatory, immunosuppressive, and especially, antirheumatic activities. Thus, according to another aspect of the present invention, there is provided a pharmaceutical composition comprising a compound of formula (I) or (II) or a salt thereof as defined hereinabove, in combination with a pharmaceutically acceptable inert carrier, such compound being present in therapeutically effective amount.

PHARMACOLOGICAL PROPERTIES

Test Compounds:

A: 3-Benzyl-5-(p-chlorobenzamido)-6,6-dimethyl-2-thioxo-tetrahydro-2H-1,3-thiazin-4-one B: 5-(p-Chlorobenzamido)-3-(2-dimethylaminoethyl)-6,6-dimethyl-2-thioxotetrahydro-2H-1,3-thiazin-4-one C: 5-(p-Chlorobenzamido)-3-(2-dimethylaminoethyl)-6,6-dimethyl-2-thioxotetrahydro-2H-1,3-thiazin-4-one p-toluenesulfonate D: 3-(2-Dimethylaminoethyl)-5-(p-methanesulfonamidobenzamido)-6,6-dimethyl-2-thioxo-tetrahydro-2H-1,3-thiazin-4-one p-toluenesulfonate E: N-(p-Chlorobenzoyl)-S-(2-dimethylaminoethylthiocarbamoyl)-penicillamine Acetylsalicylic Acid (for comparison)

D-Penicillamine (for comparison)

METHODS:

(1) Leukocyte migration in the rat

The test was performed according to the method described by H. Ishikawa et al in "Yakugaku Zasshi (Journal of the Pharmaceutical Society of Japan)", vol. 88, 1472 (1968).

Male Donryu rats weighing about 150 g were divided into groups of 4 to 5 animals each. Five ml of 2% suspension of carboxymethylcellulose (CMC) in physiological saline, which was treated by autoclaving at 120° C. for 15 minutes, was injected subcutaneously in the supra-scapular area. Five and 7 hours later, 0.1 ml of fluid in the CMC pouch was collected and mixed with 3 ml of 0.02% brilliant cresyl blue solution in phosphate buffer (0.002M, pH 7.0). The suspension was put in a Burker chamber and the emigrating leukocytes were counted under a microscope (magnification 400x). The percent inhibition was calculated as compared with the count in the control group. Compounds tested were administered into the CMC pouch immediately after the injection of the CMC suspension.

(2) Assay of release of lysosomal enzymes from polymorphonuclear (PMN) leukocytes or macrophages during phagocytosis Preparation of rat PMN leukocytes was carried out according to the method described by M. Nakanishi et al in "Yakugaku Zasshi (Journal of the Pharmaceutical Society of Japan)", vol. 95, 1027 (1975).

Preparation of rat peritoneal macrophages was carried out according to the method described by D. Gemsa et al in "Journal of Clinical Investigation", vol. 52, 812 (1973).

Lysosomal enzymes were released from PMN leukocytes exposed to homologous serum-treated zymosan particles (0.5–3µ in diameter, Sigma) according to the method described by M. Nakanishi et al in "Yakugaku Zasshi (Journal of the Pharmaceutical Society of Japan)", vol. 95, 672 (1975).

The effects of test compounds on the enzyme release were studied by determining the release of lysosomal marker enzymes such as aryl sulfatase.

The test compounds were dissolved in ethanol. The test solution (10 µl) or solvent (control, 10 µl) was added to a 10-ml conical flask containing 2.0 ml of the PMN leukocyte or macrophage suspension. The mixture was kept at 25° C. for 10 minutes. Immediately after the addition of 50 µl of serum-treated zymosan particles (10 mg/ml) to the above mixture, 1.0-ml aliquots were removed to determine the initial activity of free enzymes in the supernatant. The residual mixtures were incubated at 37° C. for 30 minutes with shaking at an agitation cycle of 75/min, and centrifuged at 350 g for 10 minutes at 4° C. The supernatant thus obtained was used for the measurement of the marker enzymes released from PMN leukocytes or macrophages during phagocytosis. The total activity of these enzymes was assayed using the 27,000 g supernatant obtained by centrifuging the PMN leukocytes or macrophages incubated at 37° C. for 30 minutes in 0.2% (v/v) Triton X-100 - Hanks' solution.

(3) Adjuvant induced arthritis in the rat

The test was performed according to the method described by B. B. Newbould in "British Journal of Pharmacology", vol. 21, 127 (1963).

Male Wistar rats weighing 180 to 210 g were divided into groups of 8 animals each. The arthritic syndrome was induced by an intradermal injection into the right hind paw of 0.1 ml of a suspension of dead tubercle bacilli (6 mg/ml) in liquid paraffin. Swellings in the hind feet were measured with the fluid displacement method at 4, 10, 15, 18, 21 and 28 days after the adjuvant inoculation. Compounds tested were orally administered daily from the adjuvant inoculation day (day 1) to day 20. Results:

The results are summarized in the following table.

| Test Compound | Leukocyte Migration $ED_{50}$(mg/rat) | | Secretion of Lysosomal Enzyme $IC_{20}(\mu M)$ | | Prophylactic Effect on Adjuvant Arthritis |
|---|---|---|---|---|---|
| | 5 hr | 7 hr | PMN leukocyte | Macrophage | MED (mg/kg) |
| A | 15 | 15 | 0.2 | >10 | 50 |
| B | 2 | 2 | 0.5 | 0.2 | 25 |
| C | 3.5 | 5 | 1 | 0.1 | 25 |
| D | 2 | 5 | 0.3 | 0.5 | 10 |
| E | 2.7 | 3.6 | 1 | 0.1 | 10 |
| AcetylsalicylicAcid | 20 | >25 | 0.1 | 100 | 100 |
| D-Penicillamine | >40 | >40 | 10 | 1 | >200 |

$ED_{50}$: 50% effective dose
$IC_{20}$: 20% inhibitory concentration
MED : minimum effective dose The toxicity of the compounds of the invention in mice and rats is of very low order.

In view of various tests, including those mentioned above, the compounds of the invention represented by formulas (I) and (II), in base or salt form, can be safely administered for the treatment of rheumatoid arthritis in the form of a pharmaceutical preparation with a suitable and conventional pharmaceutically acceptable carrier, without adversely affecting the patients.

The pharmaceutical preparations can take any conventional form such as tablets, capsules, granules, powders, ointments, suppositories, syrups or injectable solutions.

The following is an example of formulations when a compound of the invention is administered for pharmaceutical purposes.

50 mg tablets are prepared from the following compositions:
Compound (I) or (II) or its salt: 50 mg
Calcium Cellulose Glycolate: 50 mg
Lactose: 30 mg
Acid Treated Talc: 25 mg The daily dose of compound (I) or (II) or a salt thereof for human adults usually ranges from about 100 mg to 600 mg for oral administration, in single or multiple dose, but it may vary depending upon the age, weight, and/or severity of the conditions to be treated as well as the response to the medication.

The present invention will be better understood from the following examples, but they are not to be construed as limiting the present invention.

EXAMPLE 1

Sodium hydrogen carbonate (36 g) is added to a solution of 30.3 g of D-penicillamine ethyl ester hydrochloride in 303 ml of water and 303 ml of ethyl acetate with stirring under a nitrogen atmosphere. To the resulting mixture is added dropwise 34 g of p-methanesulfonamidobenzoyl chloride below 10° C. After addition is complete, the mixture is stirred below 10° C. for 30 minutes and then at room temperature for an additional 3 hours. The reaction mixture is then made acidic with concentrated hydrochloric acid, and the acidic solution is extracted with ethyl acetate. The extract is washed with water, and dried over magnesium sulfate. The solvent is removed under reduced pressure to give 52 g of D-N-(p-methanesulfonamidobenzoyl)penicillamine ethyl ester.

2-Dimethylaminoethyl isothiocyanate (21 g) is added to a solution of 52 g of D-N-(p-methanesulfonamidobenzoyl)penicillamine ethyl ester in 750 ml of pyridine under a nitrogen atmosphere. The resulting mixture is stirred at room temperature for 1.5 hours and then at 65°-70° C. for an additional 6 hours. The reaction mixture is then concentrated under reduced pressure, and the crude product is recrystallized from ethyl acetate to give 48 g of 3-(2-dimethylaminoethyl)-5-(p-methanesulfonamidobenzamido)-6,6-dimethyl-2-thioxo-tetrahydro-2H-1,3-thiazin-4-one as pale yellow crystals, melting at 158°-159° C. with decomposition.

This product (48 g) is dissolved in 1 liter of acetone, and 22 g of p-toluenesulfonic acid is added. The mixture is warmed until the solid melts. After cooling, the precipitate is collected by filtration, and recrystallized from acetone-methanol (3:2) to give 49 g of the corresponding p-toluenesulfonate as pale yellow crystals, melting at 181°-182° C. with decomposition.

EXAMPLE 2

2-Dimethylaminoethyl isothiocyanate (5.4 g) is added to a solution of 11 g of D-N-(p-chlorobenzoyl)-penicillamine ethyl ester in 100 ml of pyridine under a nitrogen atmosphere. The whole mixture is stirred at room temperature for 1.5 hours and then at 75° C. for an additional 6 hours. The solvent is then removed under reduced pressure, and the crude product is recrystallized from a mixture of isopropanol and ethyl acetate to give 5-(p-chlorobenzamido)-3-(2-dimethylaminoethyl)-6,6-dimethyl-2-thioxo-tetrahydro-2H-1,3-thiazin-4-one as pale yellow crystals, melting at 152°-153° C.

EXAMPLE 3

2-Diethylaminoethyl isothiocyanate (8 g) is added to a solution of 12 g of D-N-benzoyl-penicillamine ethyl ester in 160 ml of pyridine under a nitrogen atmosphere. The whole mixture is stirred at room temperature for 1.5 hours and then at 80° C. for an additional 5 hours. The solvent is then removed under reduced pressure, and the residue is crystallized from isopropyl ether. Recrystallization from isopropanol gives 5-benzamido-3-(2-diethylaminoethyl)-6,6-dimethyl-2-thioxo-tetrahydro-2H-1,3-thiazin-4-one as pale yellow crystals, melting at 152°–153° C.

EXAMPLE 4

A mixture of 7.0 g of D-N-benzoyl-penicillamine ethyl ester, 2.1 g of methyl isothiocyanate and 70 ml of pyridine is stirred at 70° C. for 2.5 hours. The solvent is then removed under reduced pressure. The residue is dissolved in 100 ml of ethyl acetate, and the solution is washed successively with 50 ml of water, 50 ml of 10% hydrochloric acid and 50 ml of water, and dried over magnesium sulfate. The solvent is removed under reduced pressure, and the residue is recrystallized from ethanol to give 5-benzamido-3,6,6-trimethyl-2-thioxo-tetrahydro-2H-1,3-thiazin-4-one as yellow crystals, melting at 184°–185° C.

EXAMPLE 5

A mixture of 4.0 g. of D-N-benzoyl-penicillamine ethyl ester, 1.2 g of methyl isothiocyanate, two drops of triethylamine and 50 ml of ethyl acetate is stirred overnight at room temperature and then under reflux for an additional 5 hours. The reaction mixture is washed with 20 ml of 1% hydrochloric acid and then with 50 ml of water, and dried over magnesium sulfate. The solvent is removed under reduced pressure, and the residue is purified by column chromatography on silica gel using benzene as an eluent. Thus is obtained 5-benzamido-3,6,6-trimethyl-2-thioxo-tetrahydro-2H-1,3-thiazin-4-one, melting at 184°–185° C.

EXAMPLE 6

Furfuryl isothiocyanate (6 g) is added to a solution of 10 g of D-N-benzoyl-penicillamine ethyl ester in 120 ml of pyridine under a nitrogen atmosphere. The whole mixture is stirred at room temperature for 1.5 hours and then at 75° C. for an additional 7 hours. The solvent is then removed under reduced pressure, and crude product is recrystallized from isopropanol to give 5-benzamido-3-furfuryl-6,6-dimethyl-2-thioxo-tetrahydro-2H-1,3-thiazin-4-one as pale yellow crystals, melting at 168°–169° C.

EXAMPLE 7

2-Thienylmethyl isothiocyanate (5.9 g) is added to a solution of 10 g of D-N-(p-chlorobenzoyl)-penicillamine ethyl ester in 150 ml of pyridine under a nitrogen atmosphere. The whole mixture is stirred at room temperature for 1.5 hours and then at 80° C. for an additional 6.5 hours. The solvent is then removed under reduced pressure, and the crude product is recrystallized from isopropanol to give 5-(p-chlorobenzamido)-6,6-dimethyl-3-(2-thienylmethyl)-2-thioxo-tetrahydro-2H-1,3-thiazin-4-one as pale yellow crystals, melting at 176°–177° C.

EXAMPLE 8

2-Dimethylaminoethyl isothiocyanate (5 g) is added to a suspension of 11 g of D-N-(p-chlorobenzoyl)-penicillamine in 100 ml of tetrahydrofuran under a nitrogen atmosphere. The resulting mixture is stirred at room temperature for 3 days. The solvent is then removed under reduced pressure below 30° C., and the residue is dissolved in chloroform. The solution is filtered, isopropyl ether is added to the filtrate, and the resulting mixture is cooled. Thus is obtained N-(p-chlorobenzoyl)-S-(2-dimethylaminoethylthiocarbamoyl)-penicillamine as white crystals, melting at 142°–143° C. with decomposition.

EXAMPLE 9

Water (10 ml) is added to a solution of 30 g of 5-(p-chlorobenzamido)-3-(2-dimethylaminoethyl)-6,6-dimethyl-2-thioxo-tetrahydro-2H-1,3-thiazin-4-one in 600 ml of ethyl acetate. The resulting mixture is stirred at room temperature for 5 days. The precipitate is collected by filtration, and washed with ethyl acetate. Thus is obtained N-(p-chlorobenzoyl)-S-(2-dimethylaminoethylthiocarbamoyl)-penicillamine as white crystals, melting at 142°–143° C. with decomposition.

EXAMPLE 10

A mixture of 10 g of N-(p-chlorobenzoyl)-S-(2-dimethylaminoethylthiocarbamoyl)-penicillamine, 2 g of glacial acetic acid and 100 ml of chloroform is stirred under reflux for 5 hours. The solvent is then removed under reduced pressure, and the crude product is recrystallized from a mixture of ethyl acetate and isopropyl ether to give 5-(p-chlorobenzamido)-3-(2-dimethylaminoethyl)-6,6-dimethyl-2-thioxo-tetrahydro-2H-1,3-thiazin-4-one as pale yellow crystals, melting at 152°–153° C.

The present invention provides such novel penicillamine compounds of formulas (I) and (II) and salts thereof as described in the following:

(1) 3-(2-Dimethylaminoethyl)-5-(-p-methanesulfonamidobenzamido)-6,6-dimethyl-2-thioxo-tetrahydro-2H-1,3-thiazin-4-one, m.p. 158°–159° C. (decomposition); its p-toluenesulfonate, m.p. 181°–182° C. (decomposition); its benzenesulfonate, m.p. 154°–155° C. (decomposition); its methanesulfonate, m.p. 151°–153° C. (decomposition)

(2) 5-(p-Chlorobenzamido)-3-(2-dimethylaminoethyl)-6,6-dimethyl-2-thioxo-tetrahydro-2H-1,3-thiazin-4-one, m.p. 152°–153° C.; its p-toluenesulfonate, m.p. 161°–162° C. (decomposition); its benzenesulfonate, m.p. 169°–170° C. (decomposition); its methanesulfonate monohydrate, m.p. 130°–132° C. (decomposition); its sulfate, m.p. 181°–182° C. (decomposition)

(3) 5-Benzamido-3-(2-diethylaminoethyl)-6,6-dimethyl-2-thioxo-tetrahydro-2H-1,3-thiazin-4-one, m.p. 152°–153° C.

(4) 5-Benzamido-3,6,6-trimethyl-2-thioxo-tetrahydro-2H-1,3-thiazin-4-one, m.p. 184°–185° C.

(5) 5-Benzamido-3-furfuryl-6,6-dimethyl-2-thioxo-tetrahydro-2H-1,3-thiazin-4-one, m.p. 168°–169° C.

(6) 5-(p-Chlorobenzamido)-6,6-dimethyl-3-(2-thienylmethyl)-2-thioxo-tetrahydro-2H-1,3-thiazin-4-one, m.p. 176°–177° C.

(7) 5-Benzamido-3-benzyl-6,6-dimethyl-2-thioxo-tetrahydro-2H-1,3-thiazin-4-one, m.p. 191°–192° C.

(8) 5-Acetamido-3,6,6-trimethyl-2-thioxo-tetrahydro-2H-1,3-thiazin-4-one, m.p. 155°–157° C.

(9) 5-Benzyloxycarbonylamino-3,6,6-trimethyl-2-thioxo-tetrahydro-2H-1,3-thiazin-4-one, m.p. 107°–109° C.

(10) 3-Benzyl-5-ethoxycarbonylamino-6,6-dimethyl-2-thioxo-tetrahydro-2H-1,3-thiazin-4-one

(11) 5-(p-Chlorobenzamido)-3-ethyl-6,6-dimethyl-2-thioxo-tetrahydro-2H-1,3-thiazin-4-one
(12) 5-Anisamido-3-(p-chlorobenzyl)-6,6-dimethyl-2-thioxo-tetrahydro-2H-1,3-thiazin-4-one, m.p. 126°-127° C.
(13) 3-(p-Methoxybenzyl)-6,6-dimethyl-2-thioxo-5-(p-toluamido)-tetrahydro-2H-1,3-thiazin-4-one, m.p. 158°-159° C.
(14) 3-Allyl-5-(m-chlorobenzamido)-6,6-dimethyl-2-thioxo-tetrahydro-2H-1,3-thiazin-4-one
(15) 3-(o-Methoxybenzyl)-6,6-dimethyl-5-propionamido-2-thioxo-tetrahydro-2H-1,3-thiazin-4-one
(16) 5-Acetamido-3-benzyl-6,6-dimethyl-2-thioxo-tetrahydro-2H-1,3-thiazin-4-one, m.p. 157°-158° C.
(17) 6,6-Dimethyl-3-(p-methylbenzyl)-5-(m-trifluoromethylbenzamido)-2-thioxo-tetrahydro-2H-1,3-thiazin-4-one
(18) 5-Benzamido-6,6-dimethyl-3-phenethyl-2-thioxo-tetrahydro-2H-1,3thiazin-4-one, m.p. 118°-119° C.
(19) 3,6,6-Trimethyl-5-phenacetamido-2-thioxo-tetrahydro-2H-1,3-thiazin-4-one
(20) 3-Benzyl-6,6-dimethyl-5-phenacetamido-2-thioxo-tetrahydro-2H-1,3-thiazin-4-one
(21) 3-Benzyl-5-benzyloxycarbonylamino-6,6-dimethyl-2-thioxo-tetrahydro-2H-1,3-thiazin-4-one, m.p. 111°-112° C.
(22) 3-(o-Chlorobenzyl)-6,6-dimethyl-5-phenacetamido-2-thioxo-tetrahydro-2H-1,3-thiazin-4-one, m.p. 173°-174° C.
(23) 3-Benzyl-5-(p-chlorobenzamido)-6,6-dimethyl-2-thioxo-tetrahydro-2H-1,3-thiazin-4-one, m.p. 195°-196° C.
(24) 3-Benzyl-6,6-dimethyl-5-propionamido-2-thioxo-tetrahydro-2H-1,3-thiazin-4-one, m.p. 158°-159° C.
(25) 3-Benzyl-6,6-dimethyl-2-thioxo-5-(p-toluamido)-tetrahydro-2H-1,3-thiazin-4-one, m.p. 195°-196° C.
(26) 3-Allyl-5-benzamido-6,6-dimethyl-2-thioxo-tetrahydro-2H-1,3-thiazin-4-one, m.p. 109°-110° C.
(27) 5-(p-Chlorobenzamido)-3-(p-methoxybenzyl)-6,6-dimethyl-2-thioxo-tetrahydro-2H-1,3-thiazin-4-one, m.p. 152°-153° C.
(28) 6,6-Dimethyl-3-(p-methylbenzyl)-2-thioxo-5-(p-toluamido)-tetrahydro-2H-1,3-thiazin-4-one, m.p. 175°-176° C.
(29) 5-Benzyloxycarbonylamino-6,6-dimethyl-3-phenethyl-2-thioxo-tetrahydro-2H-1,3-thiazin-4-one, m.p. 96°-97° C.
(30) 5-Anisamido-3-benzyl-6,6-dimethyl-2-thioxo-tetrahydro-2H-1,3-thiazin-4-one, m.p. 135°-137° C.
(31) 3-Benzyl-5-(o-chlorobenzamido)-6,6-dimethyl-2-thioxo-tetrahydro-2H-1,3-thiazin-4-one, m.p. 164°-165° C.
(32) 3-Benzyl-5-(3,4-dichlorobenzamido)-6,6-dimethyl-2-thioxo-tetrahydro-2H-1,3-thiazin-4-one, m.p. 179°-180° C.
(33) 3-Benzyl-5-(p-fluorobenzamido)-6,6-dimethyl-2-thioxo-tetrahydro-2H-1,3-thiazin-4-one, m.p. 180°-181° C.
(34) 5-(p-Chlorobenzamido)-3-(p-chlorobenzyl)-6,6-dimethyl-2-thioxo-tetrahydro-2H-1,3-thiazin-4one, m.p. 150°-151° C.
(35) 5-(p-Chlorobenzamido)-3-(p-fluorobenzyl)-6,6-dimethyl-2-thioxo-tetrahydro-2H-1,3-thiazin-4-one, m.p. 158°-159° C.
(36) 5-Benzamido-3-(p-fluorobenzyl)-6,6-dimethyl-2-thioxo-tetrahydro-2H-1,3-thiazin-4-one, m.p. 180°-181° C.
(37) 5-(p-Fluorobenzamido)-3-(p-fluorobenzyl)-6,6-dimethyl-2-thioxo-tetrahydro-2H-1,3-thiazin-4-one, m.p. 142°-143° C.
(38) 5-Benzamido-3-(p-chlorobenzyl)-6,6-dimethyl-2-thioxo-tetrahydro-2H-1,3-thiazin-4-one, m.p. 180°-181° C.
(39) 5-Benzyloxycarbonylamino-3-(p-chlorobenzyl)-6,6-dimethyl-2-thioxo-tetrahydro-2H-1,3-thiazin-4-one, m.p. 115°-116° C.
(40) 3-(p-Chlorobenzyl)-6,6-dimethyl-5-phenacetamido-2-thioxo-tetrahydro-2H-1,3-thiazin-4-one, m.p. 149°-150° C.
(41) 5-Benzyloxycarbonylamino-3-(p-fluorobenzyl)-6,6-dimethyl-2-thioxo-tetrahydro-2H-1,3-thiazin-4-one, m.p. 126°-127° C.
(42) 3-(p-Fluorobenzyl)-6,6-dimethyl-5-phenacetamido-2-thioxo-tetrahydro-2H-1,3-thiazin-4-one
(43) 5-Benzamido-3-(o-chlorobenzyl)-6,6-dimethyl-2-thioxo-tetrahydro-2H-1,3-thiazin-4-one, m.p. 189°-190° C.
(44) 5-Benzamido-3-(m-chlorobenzyl)-6,6-dimethyl-2-thioxo-tetrahydro-2H-1,3-thiazin-4-one
(45) 5-Benzamido-3-(3,3-diphenylpropyl)-6,6-dimethyl-2-thioxo-tetrahydro-2H-1,3-thiazin-4-one, m.p. 173°-174° C.
(46) 3-Benzyl-5-decanamido-6,6-dimethyl-2-thioxo-tetrahydro-2H-1,3-thiazin-4-one, m.p. 101°-102° C.
(47) 3-Benzyl-5-cinnamamido-6,6-dimethyl-2-thioxo-tetrahydro-2H-1,3-thiazin-4-one, m.p. 152°-153° C.
(48) 3-Benzyl-6,6-dimethyl-5-(p-nitrobenzamido)-2-thioxo-tetrahydro-2H-1,3-thiazin-4-one, m.p. 176°-206° C.
(49) 5-(p-Chlorobenzamido)-6,6-dimethyl-3-(3,4-methylenedioxybenzyl)-2-thioxo-tetrahydro-2H-1,3-thiazin-4-one, m.p. 151°-152° C.
(50) 3-(p-Chlorobenzyl)-5-cinnamamido-6,6-dimethyl-2-thioxo-tetrahydro-2H-1,3-thiazin-4-one
(51) 5-Cinnamamido-3-(p-fluorobenzyl)-6,6-dimethyl-2-thioxo-tetrahydro-2H-1,3-thiazin-4-one, m.p. 154°-155° C.
(52) 5-Benzamido-6,6-dimethyl-3-[2-(2-pyridyl)ethyl]-2-thioxo-tetrahydro-2H-1,3-thiazin-4-one, m.p. 170°-171° C.
(53) 5-Benzamido-6,6-dimethyl-3-(pyridylmethyl)-2-thioxo-tetrahydro-2H-1,3-thiazin-4-one, m.p. 168°-169° C.
(54) 5-(p-Chlorobenzamido)-6,6-dimethyl-3-(3-pyridylmethyl)-2-thioxo-tetrahydro-2H-1,3-thiazin-4-one, m.p. 163°-164° C.
(55) 5-Decanamido-3-furfuryl-6,6-dimethyl-2-thioxo-tetrahydro-2H-1,3-thiazin-4-one, m.p. 111°-112° C.
(56) 5-(p-Chlorobenzamido)-3-furfuryl-6,6-dimethyl-2-thioxo-tetrahydro-2H-1,3-thiazin-4-one, m.p. 199°-200° C.
(57) 5-(p-Fluorobenzamido)-3-furfuryl-6,6-dimethyl-2-thioxo-tetrahydro-2H-1,3-thiazin-4-one, m.p. 174°-175° C.
(58) 5-Anisamido-3-furfuryl-6,6-dimethyl-2-thioxo-tetrahydro-2H-1,3-thiazin-4-one, m.p. 135°-136° C.
(59) 5-(3,4-Dichlorobenzamido)-3-furfuryl-6,6-dimethyl-2-thioxo-tetrahydro-2H-1,3-thiazin-4-one, $n_D^{20}$ 1.5811.
(60) 5-Benzamido-6,6-dimethyl-3-(2-thienylmethyl)-2-thioxo-tetrahydro-2H-1,3-thiazin-4-one, m.p. 199°-200° C.

(61) 5-(p-Chlorobenzamido)-6,6-dimethyl-3-[2-(2-pyridyl)ethyl]-2-thioxo-tetrahydro-2H-1,3-thiazin-4-one

(62) 5-Acetamido-6,6-dimethyl-3-[2-(2-pyridyl)ethyl]-2-thioxo-tetrahydro-2H-1,3-thiazin-4-one

(63) 5-Benzyloxycarbonylamino-6,6-dimethyl-3-(2-thienylmethyl)-2-thioxo-tetrahydro-2H-1,3-thiazin-4-one

(64) 6,6-Dimethyl-3-(2-thienylmethyl)-2-thioxo-5-(p-toluamido)-tetrahydro-2H-1,3-thiazin-4-one

(65) 3-Furfuryl-6,6-dimethyl-5-(p-nitrobenzamido)-2-thioxo-tetrahydro-2H-1,3-thiazin-4-one

(66) 5-Cinnamamido-3-furfuryl-6,6-dimethyl-2-thioxo-tetrahydro-2H-1,3-thiazin-4-one, m.p. 162°–163° C.

(67) 3-Furfuryl-6,6-dimethyl-2-thioxo-5-(m-trifluoromethylbenzamido)-tetrahydro-2H-1,3-thiazin-4-one

(68) 5(p-Chlorobenzyloxycarbonylamino)-3-furfuryl-6,6-dimethyl-2-thioxo-tetrahydro-2H-1,3-thiazin-4-one

(69) 5-Ethoxycarbonylamino-3-furfuryl-6,6-dimethyl-2-thioxo-tetrahydro-2H-1,3-thiazin-4-one

(70) 5-Benzamido-3-(3-dimethylaminopropyl)-6,6-dimethyl-2-thioxo-tetrahydro-2H-1,3-thiazin-4-one, m.p. 117°–118° C.

(71) 5-Benzamido-6,6-dimethyl-3-(2-morpholinoethyl)-2-thioxo-tetrahydro-2H-1,3-thiazin-4-one, m.p. 156°–157° C.

(72) 5-Benzamido-6,6-dimethyl-3-[3-(1-pyrrolidinyl)propyl]-2-thioxo-tetrahydro-2H-1,3-thiazin-4-one, m.p. 120°–121° C.

(73) 5-Benzamido-6,6-dimethyl-3-[3-(4-phenyl-1-piperazinyl)propyl]-2-thioxo-tetrahydro-2H-1,3-thiazin-4-one, m.p. 120°–121° C.

(74) 5-(p-Chlorobenzamido)-6,6-dimethyl-3-(2-morpholinoethyl)-2-thioxo-tetrahydro-2H-1,3-thiazin-4-one, m.p. 143°–146° C.

(75) 5-Benzamido-3-(2-dimethylaminoethyl)-6,6-dimethyl-2-thioxo-tetrahydro-2H-1,3-thiazin-4-one, m.p. 136°–137° C.

(76) 5-(p-Chlorobenzamido)-3-(2-diethylaminoethyl)-6,6-dimethyl-2-thioxo-tetrahydro-2H-1,3-thiazin-4-one, m.p. 143°–144° C.

(77) 5-(p-Chlorobenzamido)-6,6-dimethyl-3-[2-(4-methyl-1-piperazinyl)ethyl]-2-thioxo-tetrahydro-2H-1,3-thiazin-4-one, m.p. 137°–138° C.

(78) 5-(p-Chlorobenzamido)-3-[2-(4-(m-chlorophenyl)-1-piperazinyl)ethyl]-6,6-dimethyl-2-thioxo-tetrahydro-2H-1,3-thiazin-4-one, $n_D^{20}$ 1.5870

(79) 5-(p-Chlorobenzamido)-6,6-dimethyl-2-thioxo-3-[2-(4-(m-trifluoromethylphenyl)-1-piperazinyl)ethyl]-tetrahydro-2H-1,3-thiazin-4-one, $n_D^{20}$ 1.5581

(80) 5-(p-Chlorobenzamido)-6,6-dimethyl-3-[2-(4-phenyl-1-piperazinyl)ethyl]-2-thioxo-tetrahydro-2H-1,3-thiazin-4-one, $n_D^{20}$ 1.5978

(81) 5-(p-Chlorobenzamido)-6,6-dimethyl-3-(3-morpholinopropyl)-2-thioxo-tetrahydro-2H-1,3-thiazin-4-one, $n_D^{20}$ 1.5748

(82) 5-(p-Chlorobenzamido)-6,6-dimethyl-3-(2-piperidinoethyl)-2-thioxo-tetrahydro-2H-1,3-thiazin-4-one, m.p. 158°–159° C.

(83) 5-Benzamido-6,6-dimethyl-3-(2-piperidinoethyl)-2-thioxo-tetrahydro-2H-1,3-thiazin-4-one, m.p. 163°–164° C.

(84) 5-Benzamido-6,6-dimethyl-3-(3-piperidinopropyl)-2-thioxo-tetrahydro-2H-1,3-thiazin-4-one

(85) 5-Cinnamamido-3-(2-dimethylaminoethyl)-6,6-dimethyl-2-thioxo-tetrahydro-2H-1,3-thiazin-4-one, $n_D^{20}$ 1.6082

(86) 5-Benzyloxycarbonylamino-3-(2-dimethylaminoethyl)-6,6-dimethyl-2-thioxo-tetrahydro-2H-1,3-thiazin-4-one, m.p. 108°–109° C.

(87) 5-Cinnamamido-3-(2-diethylaminoethyl)-6,6-dimethyl-2-thioxo-tetrahydro-2H-1,3-thiazin-4-one, m.p. 169°–170° C.

(88) 5-Benzyloxycarbonylamino-3-(2-diethylaminoethyl)-6,6-dimethyl-2-thioxo-tetrahydro-2H-1,3-thiazin-4-one, m.p. 92°–93° C.

(89) 5-Benzamido-6,6-dimethyl-2-thioxo-3-[3-(4-(p-tolyl)-1-piperazinyl)-propyl]-tetrahydro-2H-1,3-thiazin-4-one

(90) 5-Benzamido-3-[3-(4-(p-methoxyphenyl)-1-piperazinyl)propyl]-6,6-dimethyl-2-thioxo-tetrahydro-2H-1,3-thiazin-4-one

(91) 3-(2-Dimethylaminoethyl)-6,6-dimethyl-2-thioxo-5-(p-toluamido)-tetrahydro-2H-1,3-thiazin-4-one

(92) 5-Anisamido-3-(2-dimethylaminoethyl)-6,6-dimethyl-2-thioxo-tetrahydro-2H-1,3-thiazin-4-one

(93) 3-(2-Dimethylaminoethyl)-6,6-dimethyl-2-thioxo-5-(m-trifluoromethylbenzamido)-tetrahydro-2H-1,3-thiazin-4-one

(95) 3-(2-Diethylaminoethyl)-6,6-dimethyl-5-(p-nitrobenzamido)-2-thioxo-tetrahydro-2H-1,3-thiazin-4-one

(96) 3-(2-Diethylaminoethyl)-5-(p-fluorobenzamido)-6,6-dimethyl-2-thioxo-tetrahydro-2H-1,3-thiazin-4-one, m.p. 139°–140° C.

(97) 5-Ethoxycarbonylamino-3(2-diethylaminoethyl)-6,6-dimethyl-2-thioxo-tetrahydro-2H-1,3-thiazin-4-one

(98) 5-(p-Chlorobenzyloxycarbonylamino)-3-(2-dimethylaminoethyl)-6,6-dimethyl-2-thioxo-tetrahydro-2H-1,3-thiazin-4-one

(99) 5-(p-Chlorophenacetamido)-3-(2-dimethylaminoethyl)-6,6-dimethyl-2-thioxo-tetrahydro-2H-1,3-thiazin-4-one (100) 3-(2-Dimethylaminoethyl)-6,6-dimethyl-5-phenacetamido-2-thioxo-tetrahydro-2H-1,3-thiazin-4-one, m.p. 115°–116° C.

(101) 5-Decanamido-3-(2-dibutylaminoethyl)-6,6-dimethyl-2-thioxo-tetrahydro-2H-1,3-thiazin-4-one (102) 5-Acetamido-3-[3(4-(m-chlorophenyl)-1-piperazinyl)propyl]-6,6-dimethyl-2-thioxo-tetrahydro-2H-1,3-thiazin-4-one (103) 5-(o-Chlorobenzamido)-3-(2-dimethylaminoethyl)-6,6-dimethyl-2-thioxo-tetrahydro-2H-1,3-thiazin-4-one, m.p. 121°–122° C.

(104) 3-(2-Diethylaminoethyl)-6,6-dimethyl-5-phenacetamido-2-thioxo-tetrahydro-2H-1,3-thiazin-4-one, m.p. 118°–119° C.

(105) 3-(2-Dimethylaminoethyl)-5-(p-fluorobenzamido)-6,6-dimethyl-2-thioxo-tetrahydro-2H-1,3-thiazin-4-one, m.p. 131°–132° C.

(106) 5-Benzyloxycarbonylamino-6,6-dimethyl-3-(2-piperidinoethyl)-2-thioxo-tetrahydro-2H-1,3-thiazin-4-one, m.p. 103°–104° C.

(107) 6,6-Dimethyl-5-phenacetamido-3-(2-piperidinoethyl)-2-thioxo-tetrahydro-2H-1,3-thiazin-4-one, m.p. 129°–130° C.

(108) 5-Cinnamamido-6,6-dimethyl-3-(2-piperidinoethyl)-2-thioxo-tetrahydro-2H-1,3-thiazin-4-one, m.p. 154°–155° C.

(109) 5-Benzamido-3-(2-dibutylaminoethyl)-6,6-dimethyl-2-thioxo-tetrahydro-2H-1,3-thiazin-4-one (110) 5-(p-Chlorobenzamido)-3-(2-dibutylaminoethyl)-6,6-dimethyl-2-thioxo-tetrahydro-2H-1,3-thiazin-4-one
(111) 5-(p-tert-butylbenzamido)-3-(2-dimethylaminoethyl)-6,6-dimethyl-2-thioxo-tetrahydro-2H-1,3-thiazin-4-one, m.p. 184°–185° C. (decomposition)
(112) 3-Benzyl-5-(p-tert-butylbenzamido)-6,6-dimethyl-2-thioxo-tetrahydro-2H-1,3-thiazin-4-one, m.p. 217°–218° C.
(113) 3-(2-Diethylaminoethyl)-5-(p-methanesulfonamidobenzamido)-6,6-dimethyl-2-thioxo-tetrahydro-2H-1,3-thiazin-4-one, m.p. 155°–156° C. (decomposition); its p-toluenesulfonate, m.p. 162°–164° C. (decomposition)
(114) 5-(p-Methanesulfonamidobenzamido)-6,6-dimethyl-3-(2-piperidinoethyl)-2-thioxo-tetrahydro-2H-1,3-thiazin-4-one, m.p. 169°–170° C. (decomposition)
(115) 3-(p-Fluorobenzyl)-5-(p-methanesulfonamidobenzamido)-6,6-dimethyl-2-thioxo-tetrahydro-2H-1,3-thiazin-4-one, m.p. 213°–214° C.
(116) 3-Benzyl-5-(p-methanesulfonamidobenzamido)-6,6-dimethyl-2-thioxo-tetrahydro-2H-1,3-thiazin-4-one, m.p. 237°–239° C.
(117) 3-Benzyl-5-(m-methanesulfonamidobenzamido)-6,6-dimethyl-2-thioxo-tetrahydro-2H-1,3-thiazin-4-one, m.p. 187°–225° C.
(118) 5-(p-Acetylbenzamido)-3-benzyl-6,6-dimethyl-2-thioxo-tetrahydro-2H-1,3-thiazin-4-one, m.p. 167°–168° C.
(119) 5-(o-Acetoxybenzamido)-3-benzyl-6,6-dimethyl-2-thioxo-tetrahydro-2H-1,3-thiazin-4-one, m.p. 162°–163° C.
(120) 5-(o-Acetoxybenzamido)-3-(2-dimethylaminoethyl)-6,6-dimethyl-2-thioxo-tetrahydro-2H-1,3-thiazin-4-one, m.p. 157°–158° C.
(121) 3-(2-Dimethylaminoethyl)-5-(p-ethanesulfonamidobenzamido)-6,6-dimethyl-2-thioxo-tetrahydro-2H-1,3-thiazin-4-one, m.p. 169°–170° C. (decomposition)
(122) 5-(p-Benzenesulfonamidobenzamido)-3-(2-dimethylaminoethyl)-6,6-dimethyl-2-thioxo-tetrahydro-2H-1,3-thiazin-4-one, m.p. 155°–156° C. (decomposition)
(123) 3-(2-Dimethylaminoethyl)-6,6-dimethyl-2-thioxo-5-(p-trifluoromethylsulfonamidobenzamido)-tetrahydro-2H-1,3-thiazin-4-one
(124) 5-Benzamido-3-ethoxycarbonylmethyl-6,6-dimethyl-2-thioxo-tetrahydro-2H-1,3-thiazin-4-one, m.p. 157°–158° C.
(125) 5-(p-Chlorobenzamido)-3-ethoxycarbonylmethyl-6,6-dimethyl-2-thioxo-tetrahydro-2H-1,3-thiazin-4-one, m.p. 160°–163° C.
(126) 3-Ethoxycarbonylmethyl-6,6-dimethyl-5-phenacetamido-2-thioxo-tetrahydro-2H-1,3-thiazin-4-one, m.p. 192°–198° C.
(127) 3-Ethoxycarbonylmethyl-6,6-dimethyl-5-(2-thienylacetamido)-2-thioxo-tetrahydro-2H-1,3-thiazin-4-one, m.p. 177°–178° C.
(128) 3-Ethoxycarbonylmethyl-5-(2-furylacetamido)-6,6-dimethyl-2-thioxo-tetrahydro-2H-1,3-thiazin-4-one, m.p. 158°–159° C.
(129) 5-Benzamido-3-(2-N-benzyl-N-methylaminoethyl)-6,6-dimethyl-2-thioxo-tetrahydro-2H-1,3-thiazin-4-one, m.p. 158°–159° C.
(130) 3-(2-N-Benzyl-N-methylaminoethyl)-5-(p-chlorobenzamido)-6,6-dimethyl-2-thioxo-tetrahydro-2H-1,3-thiazin-4-one, m.p. 132°–133° C.
(131) 5-Benzamido-6,6-dimethyl-3-(2-N-methyl-N-phenylaminoethyl)-2-thioxo-tetrahydro-2H-1,3-thiazin-4-one, m.p. 157°–159° C.
(132) 3-(2-Dimethylaminoethyl)5-(2-furancarboxamido)-6,6-dimethyl-2-thioxo-tetrahydro-2H-1,3-thiazin-4-one, m.p. 128°–129° C.
(133) 3-(2-Dimethylaminoethyl)-5-(2-thiophenecarboxamido)-6,6-dimethyl-2-thioxo-tetrahydro-2H-1,3-thiazin-4-one, m.p. 145°–146° C.
(134) 3-(2-Dimethylaminoethyl)-5-(2-furylacetamido)-6,6-dimethyl-2-thioxo-tetrahydro-2H-1,3-thiazin-4-one, m.p. 105°–106° C.
(135) 3-Benzyl-5-(2-furancarboxamido)-6,6-dimethyl-2-thioxo-tetrahydro-2H-1,3-thiazin-4-one, m.p. 210°–211° C.
(136) 3-Benzyl-6,6-dimethyl-5-(2-thiophenecarboxamido)-2-thioxo-tetrahydro-2H-1,3-thiazin-4-one, m.p. 220°–221° C.
(137) 3-Benzyl-5-(2-furylacetamido)-6,6-dimethyl-2-thioxo-tetrahydro-2H-1,3-thiazin-4-one, m.p. 142°–143° C.
(138) 3-Benzyl-6,6-dimethyl-5-(2-thienylacetamido)-2-thioxo-tetrahydro-2H-1,3-thiazin-4-one, m.p 166°–167° C.
(139) 3-Benzyl-5-(2-chloro-3-pyridinecarboxamido)-6,6-dimethyl-2-thioxo-tetrahydro-2H-1,3-thiazin-4-one, m.p. 158°–159° C.
(140) 3-Benzyl-5-(p-chlorophenoxyacetamido)-6,6-dimethyl-2-thioxo-tetrahydro-2H-1,3-thiazin-4-one, m.p. 127°–128° C.
(141) 3-Benzyl-6,6-dimethyl-5-phenoxyacetamido-2-thioxo-tetrahydro-2H-1,3-thiazin-4-one, m.p. 111°–112° C.
(142) 3-Benzyl-6,6-dimethyl-2-thioxo-5-[2-(2,4,5-trichlorophenoxy)propionamido]-tetrahydro-2H-1,3-thiazin-4-one, m.p. 154°–155° C.
(143) 3-Benzyl-6,6-dimethyl-2-thioxo-5-(2,4,5-trichlorophenoxyacetamido)-tetrahydro-2H-1,3-thiazin-4-one, m.p. 137°–138° C.
(144) 3-(2-Dimethylaminoethyl)-6,6-dimethyl-5-(α-methylphenacetamido)-2-thioxo-tetrahydro-2H-1,3-thiazin-4-one, m.p. 163°–164° C.
(145) 3-(2-Diethylaminoethyl)-6,6-dimethyl-5-(α-methylphenacetamido)-2-thioxo-tetrahydro-2H-1,3-thiazin-4-one, m.p. 115°–116° C.
(146) N-(p-Chlorobenzoyl)-S-(2-dimethylaminoethylthiocarbamoyl)-penicillamine, m.p. 142°–143° C. (decomposition)
(147) N-Benzoyl-S-(2-dimethylaminoethylthiocarbamoyl)-penicillamine, m.p. 146°–147° C. (decomposition)
(148) N-(o-Chlorobenzoyl)-S-(2-dimethylaminoethylthiocarbamoyl)-penicillamine, m.p. 165°–166° C. (decomposition)
(149) N-(p-Fluorobenzoyl)-S-(2-dimethylaminoethylthiocarbamoyl)-penicillamine, m.p. 160°–161° C. (decomposition)
(150) N-(-Furylcarbonyl)-S-(2-dimethylaminoethylthiocarbamoyl)-penicillamine, m.p. 119°–120° 1 C. (decomposition)
(151) N-(2-Thienylcarbonyl)-S-(2-dimethylaminoethylthiocarbamoyl)-penicillamine, m.p. 142°–143° C. (decomposition)
(152) N-(2-Phenylpropionyl)-S-(2-dimethylaminoethylthiocarbamoyl)-penicillamine, m.p. 72°–74° C. (decomposition)

(153) N-Benzoyl-S-(3-dimethylaminopropylthiocarbamoyl)-penicillamine, m.p. 143°–144° C. (decomposition)
(154) N-Phenylacetyl-S-(2-diethylaminoethylthiocarbamoyl)-penicillamine, m.p. 118°–119° C. (decomposition)
(155) N-Cinnamoyl-S-(2-diethylaminoethylthiocarbamoyl)-penicillamine, m.p. 103°–104° C. (decomposition)
(156) N-Benzoyl-S-(2-piperidinoethylthiocarbamoyl)-penicillamine, its hemihydrate m.p. 137°–138° C. (decomposition)
(157) N-(p-Chlorobenzoyl)-S-(benzylthiocarbamoyl)-penicillamine
(158) N-(p-Methanesulfonamidobenzoyl)-S-(2-dimethylaminoethylthiocarbamoyl)-penicillamine, m.p. 125°–126° C. (decomposition)

What is claimed is:

1. A cyclic penicillamine compound of the formula:

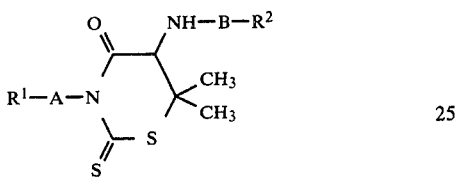

or a pharmaceutically acceptable acid addition salt thereof wherein $R^1$ represents hydrogen, $C_{1-4}$ alkyl, $C_{2-3}$ alkenyl, $C_{1-4}$ alkoxycarbonyl, phenyl, diphenylmethyl or a group of the formula: $(R^4)(R^5)N-$ wherein $R^4$ and $R^5$ represent each $C_{1-4}$ alkyl, phenyl or phenyl-$C_{1-2}$ alkyl; $R^2$ represents $C_{1-12}$ alkyl, phenyl, phenyl-$C_{1-2}$ alkyl or phenyloxy-$C_{1-2}$ alkyl; A represents alkylene of 1 to 5 carbon atoms; and B represents $-C(=O)-$ or $-C(=O)O-$; in which definitions the term "phenyl" or "phenyl-$C_{1-2}$ alkyl" in each occurrence means that it may be substituted by at least one substituent at any position(s) on the phenyl nucleus, each substituent being independently selected from $C_{1-4}$ alkyl, $C_{1-4}$ alkoxy, halogen, nitro, trifluoromethyl, methylenedioxy, $C_{2-3}$ acyl and acetoxy.

2. The compound of claim 1 wherein $R^1$ represents a group of the formula: $(R^4)(R^5)N-$ wherein $R^4$ and $R^5$ are as defined in claim 1.

3. The compound of claim 1:
5-(p-Chlorobenzamido)-3-(2-dimethylaminoethyl)-6,6-dimethyl-2-thioxo-tetrahydro-2H-1,3-thiazin-4-one or its p-toluenesulfonate or sulfate.

4. The compound of claim 1:
5-Benzamido-3-(3-dimethylaminopropyl)-6,6-dimethyl-2-thioxo-tetrahydro-2H-1,3-thiazin-4-one.

5. The compound of claim 1:
5-(o-Chlorobenzamido)-3-(2-dimethylaminoethyl)-6,6-dimethyl-2-thioxo-tetrahydro-2H-1,3-thiazin-4-one.

6. The compound of claim 1:
3-(2-Dimethylaminoethyl)-5-(p-fluorobenzamido)-6,6-dimethyl-2-thioxo-tetrahydro-2H-1,3-thiazin-4-one.

7. The compound of claim 1:
5-Benzyloxycarbonylamino-3-(2-dimethylaminoethyl)-6,6-dimethyl-2-thioxo-tetrahydro-2H-1,3-thiazin-4-one.

8. The compound of claim 1:
5-Benzamido-3-(2-dimethylaminoethyl)-6,6-dimethyl-2-thioxo-tetrahydro-2H-1,3-thiazin-4-one.

9. The compound of claim 1:
3-(2-Dimethylaminoethyl)-6,6-dimethyl-5-(2-phenylpropionamido)-2-thioxo-tetrahydro-2H-1,3-thiazin-4-one.

10. The compound of claim 1:
5-Benzamido-3-(2-diethylaminoethyl)-6,6-dimethyl-2-thioxo-tetrahydro-2H-1,3-thiazin-4-one.

11. The compound of claim 1:
3-(2-Diethylaminoethyl)-6,6-dimethyl-5-phenacetamido-2-thioxo-tetrahydro-2H-1,3-thiazin-4-one.

12. The compound of claim 1:
5-(p-Chlorobenzamido)-3-(2-diethylaminoethyl)-6,6-dimethyl-2-thioxo-tetrahydro-2H-1,3-thiazin-4-one.

13. The compound of claim 1:
3-(2-Diethylaminoethyl)-5-(p-fluorobenzamido)-6,6-dimethyl-2-thioxo-tetrahydro-2H-1,3-thiazin-4-one.

14. The compound of claim 1:
3-(2-N-benzyl-N-methylaminoethyl)-5-(p-chlorobenzamido)-6,6-dimethyl-2-thioxo-tetrahydro-2H-1,3-thiazin-4-one.

15. The compound of claim 1:
3-Benzyl-5-(p-chlorobenzamido)-6,6-dimethyl-2-thioxo-tetrahydro-2H-1,3-thiazin-4-one.

16. The compound of claim 1:
5-Benzamido-3-benzyl-6,6-dimethyl-2-thioxo-tetrahydro-2H-1,3-thiazin-4-one.

17. A pharmaceutical composition comprising the compound of claim 1 in combination with a pharmaceutically acceptable inert carrier, said compound being present in a therapeutically effective amount.

* * * * *